United States Patent [19]

Gardner

[11] Patent Number: 4,700,950

[45] Date of Patent: Oct. 20, 1987

[54] PROCESS FOR CRUSHING CANS

[76] Inventor: Ralph F. Gardner, 2115 Perth St., Toledo, Ohio 43607

[21] Appl. No.: 813,483

[22] Filed: Dec. 26, 1985

Related U.S. Application Data

[63] Continuation-in-part of Ser. No. 600,104, Apr. 13, 1984, Pat. No. 4,597,327.

[51] Int. Cl.[4] .......................... A61B 5/22; A63F 9/00

[52] U.S. Cl. .................................. 273/1 GH; 73/379; 100/902

[58] Field of Search ............... 273/1 GH, 1 G, 1 GC; 100/902; 73/379–381

[56] References Cited

U.S. PATENT DOCUMENTS 3,565,351 2/1971 Ross, Jr. ......................... 100/902 X
4,417,512 11/1983 Engelke ......................... 100/902 X
4,425,797 1/1984 Morrison ............................ 73/379
4,530,496 7/1985 Smith et al. ...................... 73/379 X
4,538,459 9/1985 Vandenbergh ................ 100/902 X

OTHER PUBLICATIONS

The Economy Baler Co. Advertising Circular Form No. EBC-136-50BS 3-1985.

*Primary Examiner*—Paul E. Shapiro
*Attorney, Agent, or Firm*—George R. Royer

[57] ABSTRACT

A process for crushing objects, primarily to crush cans, which is comprised of the steps of using manual forces assisted by resultant inertia a ramming action impacted against the device. The process involves lifting the ram, lowering it by force against the can, with a subsequent optional measurement of the can's final height after being so impacted. The process involves the measurable characteristics in degrees of offset rim alignment, as well as the quantity and quality measurements made on the layers of stratification in the crushed can's sidewalls.

2 Claims, 3 Drawing Figures

PROCESS FOR CRUSHING CANS

CROSS-REFERENCE TO RELATED APPLICATIONS

This application is a continuation-in-part of my application Ser. No. 600,104 for "An Impact Crushing Device," filed Apr. 13, 1984, now U.S. Pat. No. 4,597,327.

BACKGROUND OF INVENTION AND DISCUSSION OF PRIOR ART

This invention relates to can crushing devices powered by manual forces, as assisted by inertia structured to crush a can along its vertical axis. The use of this invention for compacting cans allows for conservation of storage space in addition to easier transportation and handling of recyclable or disposable beverage cans, once so crushed.

It is notable that the prior art patents demonstrate a general public motivation towards devices which assist in the manual compression of metal containers and specifically beverage containers. It is further seen in the more recent prior art that axial compression of cans is superior to the lateral compression devices in that a more compact shape results from the process. This is typified in the U.S. Pat. No. 4,133,261 by Belfills employing the use of a crimping bead in the process of crushing the cans.

This invention addresses itself to the act of performing axial compression with regard to a specific methodology and structure for performing such compression. The invention herein contemplates the added feature of having subsidiary sporting and entertainment value.

It is apparent that at certain locations, especially those selling canned beverages, a large volume of empty containers are generated which must be disposed of in large quantities. At many such sites, effective waste management is not economically justifiable due to sorting, storage, and personal time requirements. If, in such establishments, a means existed whereby customers assumed an active role in waste management and can disposal the very same function may be achieved in the form of sporting and entertainment, greater order of responsibility could be realized within the general public and a more ecological environment would result, all in the spirit of fun and cooperation. Thereupon, sound economic sense of recycling and waste management would be reinforced.

There is recognized in the prior art a wide variety of tools which specifically address the concept of axial compression of metal beverage containers. Forces required to perform axial compression have been achieved either through mechanical advantage and the use of side crimping or through a direct application of force in a transfer of kinetic energy by inertia and momentum. Those prior art devices which employ side crimping to assist in the breakdown of the can's sidewalls require some form of mounting bracket in which to place the can as the off-center application of force would otherwise cause the container to shift laterally in use. This aspect was reviewed by U.S. Pat. No. 4,417,512, wherein the application of a direct force grips the can as it is crushed. It is also notable that substantial forces are no longer required to crush cans due to improved technologies for design of container using thinner materials as well as a shift to the more recyclable aluminum container.

These prior art devices address trash compaction and more specifically the axial compression of beverage cans for easy storage and transportation to recycling centers. In use, however, they are likely to invade living and storage space as another piece of specialized household gadgetry. If such a can crushing device were utilized in conjunction with a sporting aspect, its use would be more acceptable.

It is to the foregoing ends and problems that the subject invention is addressed and the following objects of the subject invention are directed accordingly.

OBJECTS OF THE INVENTION

It is an object of the invention to provide a safe and efficient process for manually compressing beverage cans which provides an active and dramatic involvement of the individual performing the compression;

It is further an object of this invention to provide a handoperated can crushing process, which functions both as an entertainment and competitive medium pursuant to a set of published rules which document the activity;

It is a further object of this invention to provide a process, which can also be a sport, which is fully functional for can crushing, and also serves in promoting recycling, and conservation consistent with sporting game rules;

Yet another object of the subject invention is to provide an improved can crushing function;

Still another object of the subject invention is to provide a can crushing process that has sporting attributes as a collateral feature;

An object is to produce a can which can then be contracted and measured against standards in contexts of competition.

Other and further objects of the subject invention will become apparent from a reading of the following description taken in conjunction with the claims.

GENERAL DESCRIPTION OF THE SUBJECT INVENTION

The subject invention is a process for crushing cans including the steps of raising a vertically reciprocal ram, poised over top of a vertically upright can, lowering the ram with manually assisted force to dynamically compress the can, and then measuring the resultant compression of the can.

SPECIFIC DESCRIPTION OF THE PREFERRED EMBODIMENT

Figure 1:
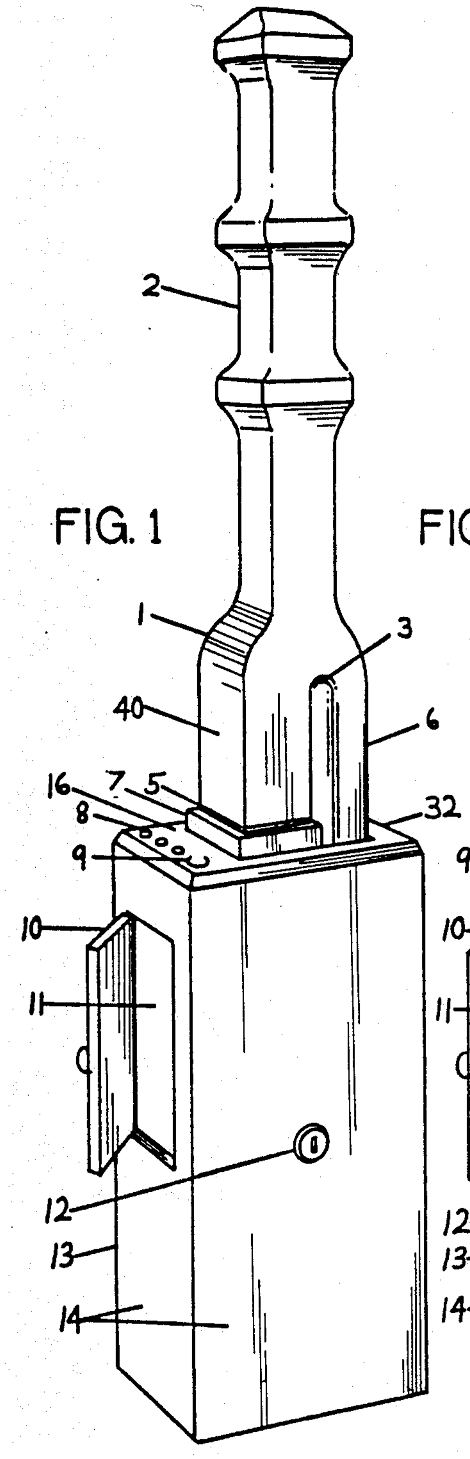
FIG. 1 is a perspective view of the can crushing device.
Figure 2:
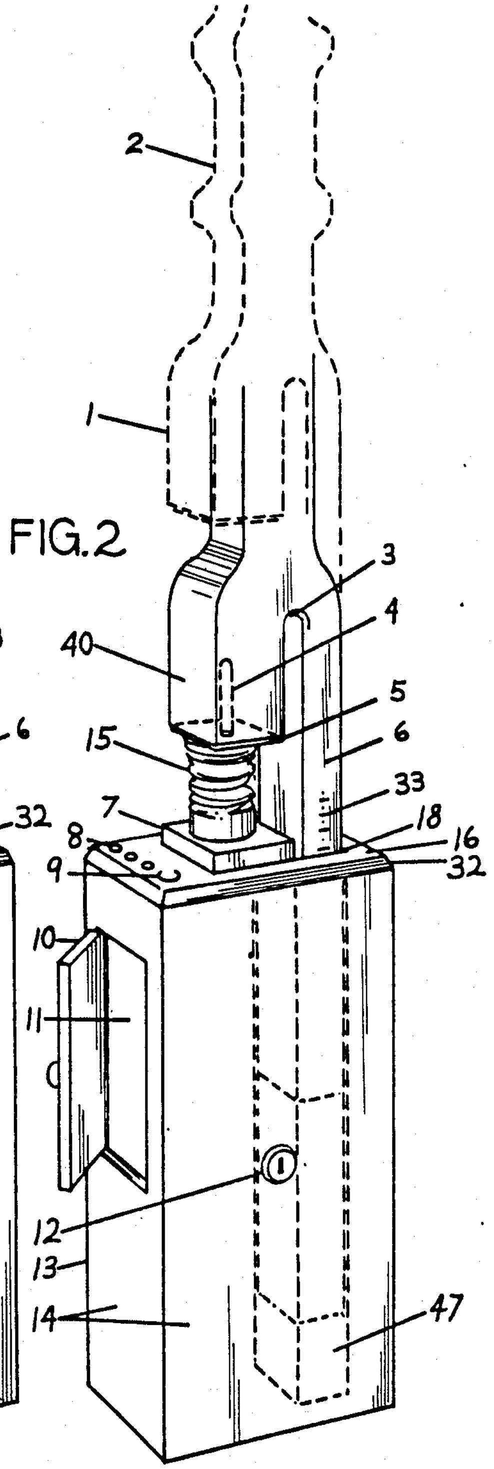
FIG. 2 is a perspective view, showing the slideable movement of the ramming apparatus as a can is being crushed on the subject device.

Turning now to the drawings in which a preferred embodiment of the subject invention is shown, FIG. 1 shows a fully-assembled can crushing device incorporating the features of the subject invention, which device is comprised of a base 13 with an elevated horizontally disposed crushing surface 7 supported on the upper horizontally disposed surface 16 of base 13. Base 13 has an optional furniture quality cabinet 14 made from either a hardwood or wood product and veneer, employing conventional woodworking or other material and crafting techniques. Front cabinet panel contains storage compartment 11 and service access door 10, all of which are optional attributes of the subject invention. Master control switch 9 and light emitting diodes 8 are recessed on the upper horizontal surface 16, as further optional characteristics.

Projecting vertically upright from the base 13 is an upright ramming assembly 1. Ramming assembly 1 is formed on its upper part with a variation of secure safe hand grasps 2 for the manual operator. Said ramming assembly 1 further has a rectangular protrusion 6 extending vertically downwardly into the base 13, as shown in the drawings. The vertically disposed slide assembly 16 is simply a female opening of parallelopiped shape which is adapted to receive in conformity fashion the parallelopiped shape of the bottom 16 of the ramming assembly.

More particularly, the ramming assembly 1 is shaped in the form of an inverted Y-shaped member, with one arm 40 of the Y being shortened relative to the longer arm 6. As shown, the longer arm 6 is parallelopiped in shape and is adapted to reciprocally slide conformingly up and down in parallelopiped opening 16 which depends vertically down into the base 13 from the upper surface 32 of base 13, as shown. The shorter arm 40 is equipped with a flat crushing surface 5 on its lower surface. This latter crushing surface functions to slam downwardly against a can placed vertically upwardly on the crushing surface 7 integrally disposed in a horizontal position in the upper surface of base 13.

The structure of the slide and weight of unit are of primary importance in effectiveness of the ramming assembly 1. Ballast 4 is installed in shorter arm 40 for purposes of establishing consistent ramming assembly weight as required in can crushing, particularly when the device is used for sporting events. Depending upon the precise materials used, the nature of this structure lends itself to standard manufacturing techniques. The ramming assembly 1 is of sufficient weight to produce an overall crushing effect upon a can positioned on the crushing surface when dropped from maximum extension, as shown in FIG. 1.

Vertical slide member 6 is adapted for slideability and enters base 13 through port 18, within channel 16. Thus, in operation as ramming assembly 1 is raised, slide 6 emerges from channel 16 to a point equal to or less than the length of the slide 6. Raising of the ramming assembly 1 produces a vertical separation between the crushing surface of the ram 5 and base crushing surface 7, demonstrating an elongation of the entire assembled crushing device.

Crushing surface 5 of ramming assembly 6 and base crushing surface 7 are produced of materials which are sufficiently abrasive for grasping mounted can during crushing process. Lower slide 6 is dimensionally compatible with internal shape of channel 16 as to restrict lateral movement and rotation of ramming assembly 1 in use of the apparatus. Accurate alignment of both crushing surfaces ram 5 and base crushing surface 7 is accomplished through the non-rotational, reciprocative nature of the slide 6.

Figure 3:
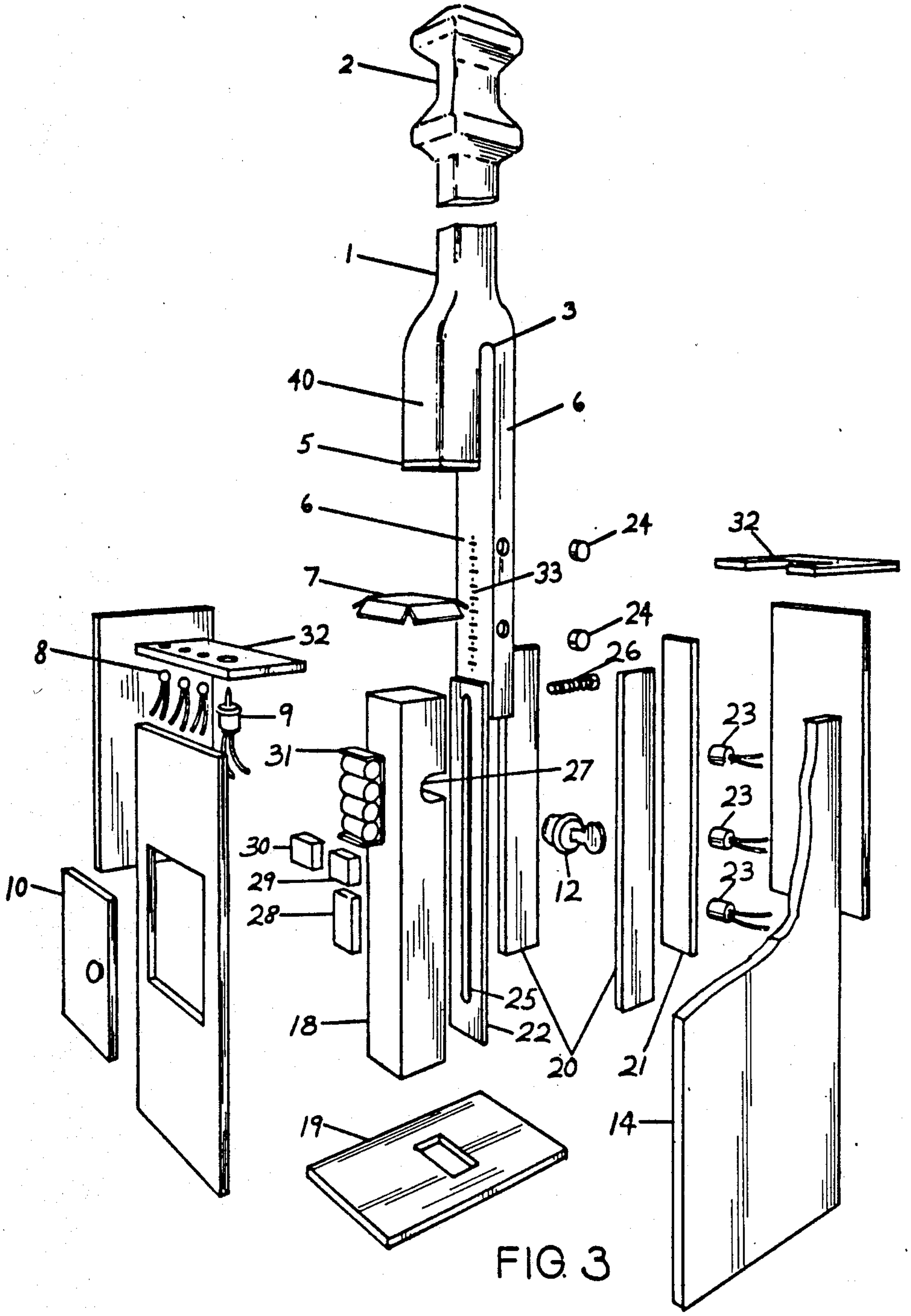
FIG. 3 is an exploded perspective view of the can crushing device depicting the simplicity of parts.

FIG. 3 shows an exploded view of the base 13 of the preferred embodiment indicating the simplicity of parts, the construction of the base and operation of the apparatus. Primary to construction of the base 13 and operation of the apparatus is a central beam 18. The function of the central beam 18 is to provide support for the base crushing surface 7 and offer resistence to the force exerted by the striking ramming assembly 1 during a typical crushing cycle. The upper end of said central beam 18 supports the base crushing surface 7. Said base crushing surface 7 has a high wear non-slip surface applied to it for purposes of mounting a can to be crushed. The non-slip surface should be manufactured or rubberized woven material, such as heavy gasket material or suitable thicknesses of softer metals such as lead alloys or copper. Other substances may demonstrate their suitability for use as a base crushing surface 7. In all cases, the base crushing surface 7 is calibrated for proper alignment of the can during competitive can crushing events.

A shock absorbing foot 19 is located on the lower end of the central beam 18 and the central beam 18 is mounted flexibly to the base, thus allowing for compression of the shock absorber 19 during the crushing cycle.

Two channel sidewalls 20, a channel end-wall 21 and the inside front channel wall 22 together from the interior of the channel, as seen in FIG. 3. Mounted within the channel end-wall 21 are electrical switches 23 actuated by their magnetic counterparts 24 embedded in the slide 6. An elongated slot 25 is defined on the inside front channel wall 22 extending the length of the channel ending near the top of base. Installed in the lower end of the slide 6 entering slot 25 is safety locking lug 26 which thwarts easy disassembly of the two major parts of the can crusher apparatus. Maximum stroke extension is achieved when safety locking lug 26 of slide 6 contacts the upper end of the elongated slot 25 within front channel wall 22. These latter times are optional.

The locking mechanism 12 is mounted in an apparatus 27 in the central base 18. An optional speaker unit 28 is mounted on the central base 18 immediately below the solid state sound generator 29 and the shock alarm switch 30. The battery box 31 is mounted on the central beam 18 where access is available through the access door 10.

Light emitting diodes 8 are mounted in the top trim surface 32, as optional appendages. Wires supplying proper output to these fixtures travel between the output light emitting diodes 8 and speaker 28 through the electric logic 29 and the electrical switches 23 located on the chanel end-wall 21. Thus, when the operator raises the ramming assembly 1, electrical pulses from the switches 23 are sent to the light emitting diodes 8. Additionally, striking the crushing surface 7 with sufficient force actuates the impact switch 30 generating sounds per the solid state circuitry 29 through speaker 28. A master switch 9 is located in the top trim surface 32 to enable or disable the electrical attractions of the can crushing apparatus. These latter electrical devices provide a measurement basis for the subject device under circumstances where the subject device is used as a competitive or sporting mechanism. More particularly, the electrical system is structured to provide a measurement of the can height after being crushed which is transmitted by electrical signals to the electrical lights shown. This latter feature enables the user to participate in a competitive manner. For this purpose, along all surfaces of the slide 6 and readily visible are the specific markings of a scale slide calibration 33. Such calibration is provided for accurate judgment of stroke extension for use by operator and observation during competitive crushing event.

The process of crushing the cans, using the subject method, thus comprises the steps of employing a vertically reciprocal ram, by raising said ram upwardly above a vertically positioned can, lowering said ram with a vertically downwardly propelled manual force, and with said downward force a portion of the ram strikes the can on its top most portion causing the can to be flattened or vertically compressed in the process. A final step can then be the measurement of the degree that the can is compressed, in linear height measurement, for sporting or competitive purposes. Measurement is further based on measurement of offset in the rim alignment and the number of layers of horizontal wrinklelike or patterned stratification along sidewalls of the can.

While a preferred embodiment of the subject invention has been described, it is not to be constructed as limiting the scope of the following claims.

I claim:

1. A process for compressing cans in a competitive process comprising the steps of:

(a) raising a vertically reciprocal ram above a vertically positioned can;

(b) lowering said reciprocal ram in a vertically downwardly manually propelled force to have a portion of the ram impact against the top of the vertically positioned can so as to compress said can;

(c) measuring the resultant compressed height of the can.

2. A process and methodology for compressing cans which is competitive in nature, structured to a methodology for playing a game:

(a) raising a slideable reciprocal ram with respect to vertically positioned can;

(b) energizing said ram with a manually propelled force to have a portion of the ram impact against the top of the positioned can so as to compress said can;

(c) measuring the resultant compressed height of the can, counting layers of stratification along can's sidewalls and measuring degrees of offset in the crushed can's rim alignment.

* * * * *